United States Patent [19]

Tenud

[11] 4,021,480
[45] May 3, 1977

[54] PROCESS FOR THE PRODUCTION OF CARNITINE

[75] Inventor: Leander Tenud, Visp, Wallis, Switzerland

[73] Assignee: Lonza Ltd., Gampel, Switzerland

[22] Filed: Sept. 25, 1975

[21] Appl. No.: 616,848

[30] Foreign Application Priority Data

Sept. 25, 1974 Switzerland .................. 12970/74

[52] U.S. Cl. .................. 260/534 M; 260/482 R; 260/632 A
[51] Int. Cl.² .................. C07C 99/00
[58] Field of Search .................. 260/534 M

[56] References Cited

UNITED STATES PATENTS

| | | | |
|---|---|---|---|
| 2,530,627 | 11/1950 | Pfister et al. | 260/534 M |
| 2,933,522 | 4/1960 | Cramer et al. | 260/534 M |
| 3,038,007 | 6/1962 | Reeve | 260/534 M |
| 3,135,788 | 6/1964 | Noguchi et al. | 260/534 M |

OTHER PUBLICATIONS

D'Alo et al., "Chem. Abstracts," vol. 60 (1964), Cols. 10777, 10778.

Primary Examiner—Joseph E. Evans
Attorney, Agent, or Firm—Fisher, Christen & Sabol

[57] ABSTRACT

The process for the production of carnitine hydrochloride which involves reacting an ester of γ-halo-acetoacetic acid having the formula:

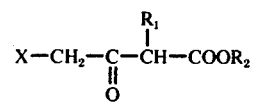

$R_1$ is a hydrogen, $R_2$ is a lower alkyl group having 1 to 10 carbon atoms and X is halogen selected from the group consisting of chlorine or bromine, with an alkali alcoholate, which is present in a stoichiometrically excessive amount. at a temperature between 0° and −40° C. The reaction product is reacted with trimethylamine at a temperature between 10° and 50° C., a (3-carbalkoxy-2-oxopropyl)-trimethyl ammonium halide resulting. The (3-carbalkoxy-2-oxopropyl)-trimethyl ammonium halide is hydrogenated, a carnitine ester resulting. Then the carnitine ester is converted by means of aqueous hydrochloride acid into carnitine hydrochloride.

14 Claims, No Drawings

PROCESS FOR THE PRODUCTION OF CARNITINE

BACKGROUND OF THIS INVENTION

1. Field of This Invention

This invention relates to a process for the production of carnitine hydrochloride.

2. Prior Art

It is known to produce carnitine from acetoacetic ester. At the same time bromoacetoacetic ester is produced by bromation, the latter is converted by means of $NaBH_4$ to $\beta$-hydroxy-$\gamma$bromobutyric acid ester. The latter is reacted with trimethylamine and the developing $\gamma$-trimethylammonium-$\beta$-hydroxybutyric acid ester bromide is saponified into carnitine hydrochloride [F. D'Alo and A. Masserini, Chemical Abstracts, Vol 60, 10777 g (1964)]. Because of the reduction with sodiumborohydride, this synthesis will probably remain limited for economic reasons merely to laboratory scale; moreover the yields are low.

It is known to use epichlorohydrin as a starting material. In such case, one proceeds in such a way that epichlorohydrin is first of all reacted with trimethylaminehydrochloride, the reaction product is converted with NaCN into the carnitine nitrile chloride and the latter is hydrolyzed to carnitine (see U.S. Pat. No. 3,135,788. In such process the products of all the intermediate steps are isolated. The yield amounts to about 74 percent.

The proposal has also been made to convert $\gamma$-chloroacetoacetic acid anilide by reaction with trimethyl amine in an organic solvent, e.g., ethanol, into $\gamma$-trimethyl ammonium acetoacetic acid anilide chloride, to hydrogenate the latter to $\gamma$-trimethyl ammonium $\beta$-hydroxy-butyric acid anilide chloride and then to convert the latter by means of aqueous hydrochloric acid into carnitine hydrochloride. A disadvantage of such a process lies in the fact that one must start out with $\gamma$-chloroacetoacetic acid anilide, which must be produced in a preliminary step from $\gamma$-chloroacetoacetic acid chloride. If in such a process one uses, instead of $\gamma$-chloroacetoacetic acid anilide, $\gamma$-chloroacetoacetic ester, then a mixture of various products develops, that is, mainly trimethylaminohydrochloride and succinylosuccinic acid ester.

BROAD DESCRIPTION OF THIS INVENTION

An object of this invention is to produce carnitine hydrochloride in a good yield by means of a multi-step process that does not require isolation of the products of the intermediate steps of such process. Other objects and advantages of this invention are set out herein or are obvious to one ordinarily skilled in the art herefrom. This invention achieves such objects and advantages.

It has now been found that very good yields of carnitine can be obtained from $\gamma$-halo acetoacetic ester, if the starting product is enolized.

This invention involves a process for the production of carnitine hydrochloride which includes reacting an ester of $\gamma$-halo-acetoacetic acid having the formula: hydrogenated, carnitine

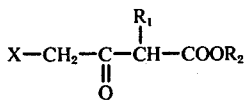

wherein $R_1$ is hydrogen atom, $R_2$ is a lower alkyl group having 1 to 10 carbon atoms and X is a halogen atom selected from the group consisting of chlorine or bromine, with an alkali alcoholate, which is present in a stoichiometrically excessive amount, at a temperature between 0° and −40° C. The reaction product is reacted with trimethylamine at a temperature between 10° and 50° C., a (3-carbalkoxy-2-oxopropyl)-trimethyl ammonium halide resulting. The (3-carbalkoxy-2-oxopropyl)-trimethyl ammonium halide is hydrogen, a carnitine ester resulting. Then the caritine ester is converted by means of aqueous hydrochloric acid into said carnitine hydrochloride, which has the formula:

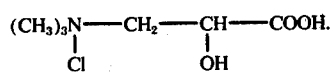

The process of this invention is distinguished by the fact, that it is a so called "one course" process, that is to say the products of the individual steps do not need to be isolated.

DETAILED DESCRIPTION OF THIS INVENTION

The process of this invention is characterized by the fact that $\gamma$-haloacetoacetic ester is converted with alkali alcoholates at an excess of more than the stoichiometric quantity into alcohol at a temperature from 0° to −40° C., the product is treated with trimethyl amine at a temperature of 10° to 50° C, the developed (3-carbaloxy-2-oxopropyl)-trimethyl ammonium chloride is hydrogenated, and the resultant carnitine ester is converted by means of aqueous hydrochloride acid into carnitine hydrochloride.

Examples of useful $\gamma$-haloacetoacetic esters, where $R_1$ is a hydrogen atom, are the methyl ester of $\gamma$-chloroacetoacetic acid, the ethyl ester of $\gamma$-chloroacetoacetic acid, the n-propyl ester of $\gamma$-chloroacetoacetic acid, the isopropyl ester of $\gamma$-chloroacetoacetic acid, the n-butyl ester of $\gamma$-chloroacetoacetic acid, the isopentyl ester of $\gamma$-chloroacetoacetic acid, the n-hexyl ester of $\gamma$-chloroacetoacetic acid, the n-decyl ester of $\gamma$-chloroacetoacetic acid, the 4-methyl-1-heptyl ester of $\gamma$-chloroacetoacetic acid, the 2,3-dimethyl-1-butyl ester of $\gamma$-chloroacetoacetic acid, the methyl ester of $\gamma$-bromoacetoacetic acid, the ethyl ester of $\gamma$-bromoacetoacetic acid, the n-propyl ester of $\gamma$-bromoacetoacetic acid, the n-hexyl ester of $\gamma$-bromoacetoacetic acid, the isopropyl ester of $\gamma$-bromoacetoacetic acid, the isohexyl ester of $\gamma$-bromoacetoacetic acid, the ethyl ester of $\gamma$-fluoroacetoacetic acid, and the ethyl ester of $\gamma$-iodoacetoacetic acid.

Preferably the $\gamma$-haloacetoacetic ester is a $\gamma$-chloroacetoacetic ester. The preferred esters moieties have 1 to 4 carbon atoms.

Preferably 1.1 to 2.0 equivalents (moles) of alkali alcoholate are used per equivalent (mole) of $\gamma$-haloacetoacetic ester.

The alkali alcoholate has the formula:

ROG or (RO)$_2$G wherein R is a lower alkyl group having 1 to 10 carbon atoms and G is an alkali moiety.

The term alkali, as used herein, means the alkali metals, such as, potassium, sodium (preferred), lithium rubidium, cesium and francium, and the alkaline earth metals, such as, barium, calcium, strontium, radium and magnesium.

Examples of useful alkali alcoholates are sodium methoxide, sodium ethoxide, sodium pentoxide, barium ethoxide, calcium methoxide, magnesium methoxide, magnesium ethoxide, potassium methoxide, sodium isobutoxide, sodium 1-decoxide, barium propoxide, sodium isohexoxide, barium butoxide, sodium-n-heptoxide, calcium propoxide, sodium propoxide, calcium pentoxide, potassium isopropoxide, potassium isoamoxide, lithium ethoxide and potassium 2-methyl-1-pentoxide. Sodium ethoxide (or sodium ethylate) is preferred.

The alkali alcoholate can be prepared using any convenient method. Alkalis, e.g., sodium, potassium, and magnesium, react with methanol to give alkali methoxides. Most alkalis, e.g., sodium, barium and calcium, react with ethanol to form alkali ethoxides. In general, alkalis react with alcohols to form alkali alcoholates.

R and R$_2$ can be the same or different lower alkyl group containing one to 10 carbon atoms, which can be straight chain or branch chain alkyl group. (Preferably R$_2$ is a lower alkyl having 1 to 4 carbon atoms and is most preferably methyl, ethyl, propyl or butyl - ethyl is most preferred). Examples of useful alkyl groups which R and R$_2$ can be are: methyl, ethyl, n-propyl, isopropyl, n-butyl, isobutyl, n-pentyl, isopentyl, n-hexyl, n-heptyl, n-octyl, n-nonyl, n-decyl, neo-pentyl, 2,4-dimethyl-3-pentyl, 2-heptyl, 3-heptyl, 2-methyl-2-heptyl, 3-methyl-2-heptyl, 4-heptyl, 2,6-dimethy-4-heptyl, 4-ethyl-4-heptyl, 2-methyl-1-heptyl, 4-methyl-4-heptyl, 3-methyl-1-heptyl, 4-propyl-4-heptyl, 4-methyl-1-heptyl, 2,2,3,3-tetramethyl butyl, 2,3-dimethyl pentyl, 2,2,4-trimethyl-pentyl, 2,4-dimethyl-3-ethyl-3-hexyl, 2-ethyl-hexyl, 2-butyl, t.-butyl, 2-methyl-1-butyl, 2-pentyl, 3-pentyl, 3-methyl-2-butyl, 2-methyl-2-butyl, 2-methyl-1-pentyl, 3-methyl-1-pentyl, 4-methyl-1-pentyl, 2-ethyl-1-butyl, t.amyl, 2,3-dimethyl-1-butyl, 2-hexyl, 3-hexyl, 3-methyl-2-pentyl, 2,2-dimethyl-3-butyl, 4-methyl-2-pentyl, 2,3-dimethyl-2-butyl, 2-methyl-3-pentyl, and 3-methyl-3-pentyl and 3-methyl-2-pentyl.

The trimethylamine reaction is preferably done at a temperature between 20° and 70° C.

The trimethyl amine is preferably used in an excess (effectively in an excess of 1 to 10 moles per mole of other reactant) and most preferably in an amount of 1.5 to 2.5 moles per mole of other reactant. After the conversion, the excess trimethylamine is distilled off. At the same time, one part of common salt is already precipitated. Subsequently, preferably gaseous hydrochloric acid up to a pH value of the solution of 7 to 5 is introduced, whereby the common salt is precipitated out almost quantitatively and can be filtered off.

Preferably the reaction of the γ-haloacetoacetic acid ester with the alkali alcoholate, the trimethylamine reaction and the hydrogenation reaction are conducted in water or in an organic solvent or suspension agent. Examples of such organic solvents or suspension agents are alcohols, such as, methanol, ethanol, isopropanol, propanol and butanol, acetonitrile, dimethyl sulfoxide and dimethyl formamide.

Preferably gaseous hydrochloric acid up to a pH value of 4 to 8 is introduced prior to hydrogenation.

The hydrogenation is preferably carried out either in an alcoholic solution or in water.

In a first subembodiment, in the hydrogenation is preferably carried out catalytically, and most preferably using hydrogen and using platinum on activated charcoal, nickel (Raney nickel) or ruthenium on activated charcoal. Preferably the temperatures for the hydrogenation lie between 0° and 70° C. In the case where Pt or Ru is used, the temperature preferably lies between (and above) 0° and 30° C., and in the case of where Ni is used, the temperature preferably lies between 40° and 70° C. H$_2$ pressures of up to (and above) 100 atm. are used for the hydrogenation. Preferably an H$_2$ pressure of 2 to 50 atm. is used for the hydrogenation.

In a second subembodiment, after the alcohol is removed the hydrogenation is carried out in water at a pH value of 4 to 8, at a temperature of 0° to 30° C. and at a H$_2$ pressure of up to 100 atm. (preferably between 2 and 20 atm.).

In this specification, including the claims, all parts, ratios, weights and proportions are on a weight basis, unless otherwise stated or unless otherwise obvious to one ordinarily skilled in the art.

EXAMPLE 1

In a 1 liter Schmizo double-walled flask with outlet pipe, equipped with a dripping funnel, stirrer and thermometer, 873 ml of a 1.260 molar sodium alcoholate solution (1.10 mole) was prepared, with exclusion of moisture, and was cooled to −25° C. 166.42 gm. of γ-chloroacetoacetic ester was diluted with 200 ml of absolute alcohol (ethanol) and was allowed to flow into the sodium alcoholate while well in a thin jet at −25° to −20° C. In order to have precise control of the temperature, the doublewalled flask was connected to a cryometer. A bright yellow enolate solution resulted.

In a 2 liter three-necked flask, 545.6 gm. of trimethyl amine (TMA) was put up in ethanol and the bright yellow enolate solution was added quickly. The mixture was heated to 50° C. by means of a warm water bath. About 1 liter of ethanol was sucked off on a rotavapor for the removal of the excess TMA. The heterogeneous reaction mixture was adjusted to pH 5 by means of hydrochloric acid gas. 10 to 20 gm. of Celite was introduced into the reaction mixture and filtered. The filtrate was concentrated on a rotavapor, whereby (3-carbethoxy-2-oxopropyl)-trimethyl ammonium chloride began to crystallize out of the alcohol solution. The crystallizate was drained off and the Celite was washed out. The filtrate was evaporated and additional (3-carbethoxy-2-oxopropyl) trimethyl ammonium chloride was precipitated with acetone. These various fractions had melting points between 165° and 170° C. 191.2 gm of this raw product corresponded to a yield of 85.5 percent.

10.0 gm. of (3-carbethoxy-2-oxopropyl) trimethyl ammonium chloride, 150 ml of absolute methanol and 2.0 gm. of platinum on activated charcoal were placed in a laboratory autoclave, were rinsed with nitrogen and subsequently with nitrogen and subsequently with hydrogen. The mixture was then hydrogenated during 14.5 hours at 40 atm., 40° C. (rotary thermostat) and a stirring velocity of 750 rpm. The catalyst was filtered off and was washed with 4 times with 20 ml of ethanol. The filtrate was evaporated on a rotavapor.

Subsequently the filtrate was reacted with aqueous hydrochloric acid, was boiled at reflux for 4 hours and was precipitated to dryness. The residue was dried for 14 hours in high vacuum at 60° C. After that, the residue was treated with 30 ml of ethanol/isopropanol (1:1) and was filtered — the filtrate evaporated. The crystalline carnitine hydrochloride was dried for 5 hours in high vacuum at 45° C. Carnitine hydrochloride at a yield of 85.9 percent related to the starting γ-chloroacetoacetic ester, was obtained.

What is claimed is:

1. The process for the production of carnitine hydrochloride which comprises (a) reacting an ester of γ-haloacetoacetic acid having the formula:

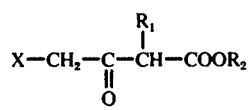

wherein $R_1$ is hydrogen, $R_2$ is a lower alkyl group having 1 to 10 carbon atoms and X is a halogen atom selected from the group consisting of chlorine or bromine, with an alkali alcoholate, which is present in a stoichiometrically excessive amount, at a temperature between 0° and −40° C; (b) reacting the reaction product of step (a) with trimethylamine at a temperature between 10° and 50° C., a (3-carbalkoxy-2-oxopropyl)-trimethyl ammonium halide resullting; (c) catalytically hydrogenating said (3-carbalkoxy-2-oxopropyl)-trimethyl ammonium halide, a carnitine ester resulting; and (d) converting said carnitine ester by means of aqueous hydrochloride acid into said carnitine hydrochloride, which has the formula:

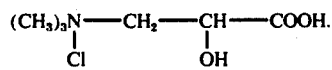

2. The process as described in claim 1 wherein said reaction step (a) is conducted in the presence of an organic solvent or suspension agent or of water.

3. The process as described in claim 1 wherein between 1.1 and 2.0 moles of said alkali alcoholate are used per mole of said γ-haloacetoacetic ester.

4. The process as described in claim 1 wherein 1 to 10 moles of said trimethyl amine is used per mole of said reaction product of step (a).

5. The process as described in claim 1 wherein 1.5 to 2.5 moles of said trimethyl amine is used per mole of said reaction product of step (a).

6. The process as described in claim 1 wherein, between step (b) and step (c), any excess trimethyl amine is distilled off.

7. The process as described in claim 1 wherein, before said hydrogenation step (c), gaseous hydrochloric acid up to a pH of 4 to 8 is introduced.

8. The process as described in claim 1 wherein said hydrogenation step (c) is carried out in alcohol with hydrogen and platinum on activated charcoal at a temperature between 0° and 70° C. and with an $H_2$ pressure of 2 to 50 atm.

9. The process as described in claim 1 wherein said hydrogenation step (c) is carried out in water at a pH of 4 to 8 with hydrogen and platinum on activated charcoal at temperatures between 0° and 30° C. and with an $H_2$ pressure of 2 to 20 atm.

10. The process of claim 1 wherein said hydrogenation step (c) is conducted in the presence of an organic solvent or suspension agent or of water.

11. The process of claim 1 wherein said hydrogenation catalyst is platinum on activated charcoal.

12. The process of claim 1 wherein said hydrogenation step (c) is conducted at a temperature between 0° and 70° C.

13. The process of claim 1 wherein said hydrogenation step (c) is conducted at a $H_2$-pressure between 2 and 50 atmospheres.

14. The process of claim 1 wherein said reaction step (a), said reaction step (b) and said hydrogenation step (c) are conducted in the presence of an organic solvent or suspension agent or of water.

* * * * *